United States Patent [19]

Montgomery

[11] 4,188,378

[45] Feb. 12, 1980

[54] ANTICANCER AND ANTIVIRAL ACTIVITY OF 9-β-D-ARABINOFURANOSYL-2-FLUOROADENINE

[75] Inventor: John A. Montgomery, Birmingham, Ala.

[73] Assignee: The United States of America as represented by the Department of Health, Education and Welfare, Washington, D.C.

[21] Appl. No.: 866,907

[22] Filed: Jan. 4, 1978

[51] Int. Cl.$^2$ ............................................. A61K 31/70
[52] U.S. Cl. ....................................... 424/180; 536/26
[58] Field of Search ...................... 536/24, 26; 424/180

[56] References Cited

U.S. PATENT DOCUMENTS

| | | | |
|---|---|---|---|
| 3,501,456 | 3/1970 | Shen et al. | 536/24 |
| 4,069,382 | 1/1978 | Baker et al. | 536/24 |

FOREIGN PATENT DOCUMENTS 1386585  3/1975  United Kingdom ...................... 536/24

OTHER PUBLICATIONS

Brockman, R. W., et al., Biochem. Pharmacol. 26, 2193-2196, (1977).

*Primary Examiner*—Johnnie R. Brown
*Assistant Examiner*—Blondel Hazel
*Attorney, Agent, or Firm*—John S. Roberts, Jr.

[57] ABSTRACT

A method of utilizing 9-β-D-arabinofuranosyl-2-fluoroadenine, known as 2-F-AraA (NSC 118218), in the treatment of murine leukemia and as an antiviral agent for DNA viruses, such as DNA viruses Herpes Simplex Virus Type I and Vaccinia virus grown in H.Ep-2 cells in culture. An operable dosage for utilization of 2-F-AraA is a treatment span of 1-10 days with the dosage 2-8 times per day at 8-400 mg/kg/dose. It has been further found that a single dosage on days 1, 5, and 9 based on a 10-day treatment schedule gave satisfactory results.

6 Claims, No Drawings

ANTICANCER AND ANTIVIRAL ACTIVITY OF 9-β-D-ARABINOFURANOSYL-2-FLUOROADENINE

This invention relates to a method of utilizing 9-β-D-arabinofuranosyl-2-fluoroadenine, known as 2-F-AraA (NSC 118218), in the treatment of murine leukemia and as an antiviral agent for DNA viruses, such as DNA viruses Herpes Simplex Virus Type I and Vaccinia virus grown in H.Ep-2 cells in culture (see Table 3). An operable dosage for utilization of 2-F-AraA is a treatment span of 1–10 days with the dosage of 8–400 mg/kg/dose 2–8 times per day. It has been further found that a single dosage on days 1, 5, and 9 based on a 10-day treatment schedule gave satisfactory results.

The compound 9-β-D-arabinofuranosyl-2-fluoroadenine (2-F-AraA) is represented by the following structure:

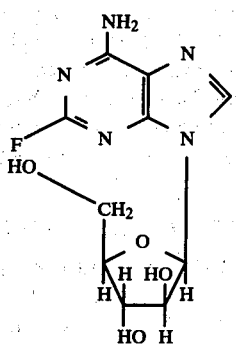

I

This compound is described in John A. Montgomery et al, "Nucleosides of 2-Fluoroadenine," J. Med. Chem., 12:498 (1969), but the broad spectrum utility of antiviral and antileukemic activity has not been described.

The parent compound to which this fluoro derivative is related is 9-β-D-arabinofuranosyladenine (AraA). This compound was found to be a potent antiviral agent in animals and in man but it has shown little potential in the treatment of leukemias. Apparently, the cause of the failure of activity in leukemias is the rapid deamination of AraA in vivo to 9-β-D-arabinofuranosylhypoxanthine (AraH), a compound with some antiviral but no antileukemic activity.

The unique feature of the present 2-F-AraA is the insertion of a fluorine atom at the 2-carbon of AraA, which makes the compound completely resistant to deamination by adenosine deaminase both in vitro and in vivo but does not interfere with its conversion to the triposphate (F-AraATP), which is as potent an inhibitor of DNA polymerase as Ara-ATP. Inhibition of DNA polymerase is considered to be responsible for the biologic activity of AraA. The levels of F-AraATP attainable in leukemia L1210 cells in mice from the administration of 2-F-AraA are much higher than the level of AraATP atainable in these cells after administration of AraA. As a result of the maintenance of these levels of the inhibitor, F-AraATP, in them, the leukemia cells are effectively destroyed in animals. At a dose of 100 mg/kg given intraperitoneally once every three hours on the first, fifth, and ninth days after implantation of the leukemic cells ($10^5$), the life span of animals dying of leukemia (4 of 6) was increased 123–155%; two animals were deemed recovered from the disease. Comparable results were obtained by administering the drug at a dose of 400 mg/kg twice a day on the first, fifth, and ninth days after implantation of leukemic cells ($10^5$). 2-F-AraA was also active against leukemia L1210 when administered by the oral route. Under similar conditions, AraA was essentially devoid of activity against this leukemia in that the leukemia cells multiplied in the presence of the drug from $10^5$ at the beginning to $3 \times 10^8$ cells at the end of treatment.

The activity of 2-F-AraA is not confined to activity against leukemia L1210, but it is also active against the P388 leukemia in mice.

2-F-AraA demonstrated activity against the DNA viruses Herpes Simplex Virus Type 1 and Vaccinia virus grown in H.Ep.-2 cells in culture.

PRIOR ART STATEMENT

John A. Montgomery et al, "Nucleosides of 2-Fluoroadenine," J. Med. Chem., 12:498 (1969).

F. Keller et al, J. Org. Chem., 32:1644 (1967). The authors describe the synthesis of Cl-AraA not 2-F-AraA.

PREPARATION OF 2-F-AraA

In this generalized preparation, the compound numbers (e.g., I, II, etc.) are coded like the more specific description in the examples which follow.

2-F-AraA is prepared by the removal of blocking groups from the sugar moiety of compounds of Formula II wherein B is a blocking group such as an aralkyl group, preferably the benzyl group. The removal may be accomplished by catalytic hydrogenolysis using a catalyst such as palladium or palladised charcoal, or by reduction with sodium and liquid ammonia according to the procedure of Montgomery and Hewson in J. Med. Chem., 12:498 (1969). The best procedure, which avoids defluorination, results from treatment of the blocked nucleoside with $BCl_3$ in methylene chloride.

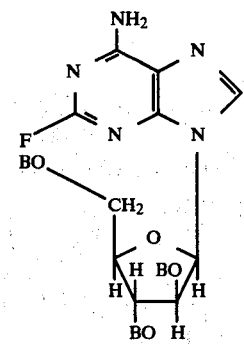

II

The compound of Formula II is prepared by the diazotization of compounds of Formula III in a mixture of 48% fluoboric acid and an organic solvent to increase the solubility of III.

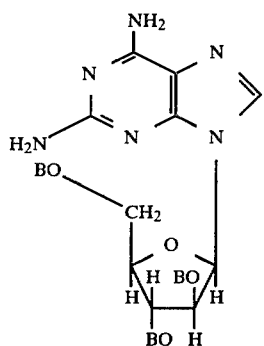

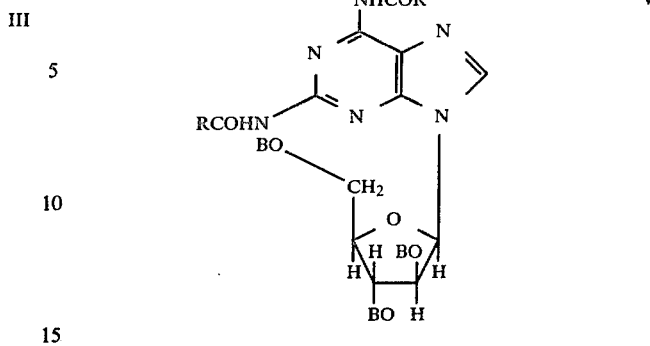

The use of chlorohydrocarbons such as chloroform results in two-phase reaction and in the formation of some 2-chloro compound by reaction of the diazonium salt with the solvent. An ether-type solvent such as tetrahydrofuran gives a homogeneous reaction that gives a purer product containing no 2-chloro compound.

The compounds of Formula III can be prepared by one of the following routes:

The reaction of Compound IV in which X is a halogen atom, preferably chlorine or bromine, with sodium azide gives the 2,6-diazido compound, which can be reduced to III catalytically with palladium, platinum, or Raney nickel catalysis.

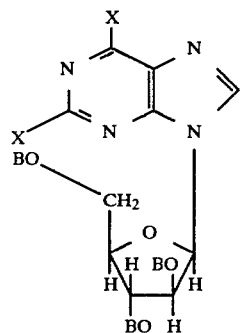

To produce IV, a dihalopurine, preferably 2,6-dichloropurine, can be condensed with an arabinofuranosyl halide blocked with removable blocking groups B, as defined herein, according to the method described by Keller et al in *J. Org. Chem.*, 32:1644 (1967). The preferred sugar is 2,3,5-tri-O-benzyl-α-D-arabinofuranosyl chloride.

Compounds of Formula V wherein R is an alkyl group of 1-8 carbon atoms can be deacylated by basic solvolysis effected, for example, by methanolic sodium methoxide or ethanolic sodium hydroxide.

Acylation of 2,6-diaminopurine, for example, with acetic anhydride in pyridine followed by reaction with an arabinofuranosyl halide blocked with removable blocking groups B gives Compound V. The sugar condensation can be carried out in a halohydrocarbon using molecular sieve as the hydrogen acceptor, or using a Lewis acid, such as $SnCl_4$, as catalyst.

Compound III can also be prepared by the reaction of the trimethylsilyl derivative of 2,6-diaminopurine with an arabinofuranosyl halide blocked with removable blocking groups B.

THE ANTITUMOR ACTIVITY

It has been noted that the antitumor activity of the parent compound, 9-β-D-arabinofuranosyladenine (AraA), is enhanced by inhibition of adenosine deaminase and inhibition of DNA synthesis in tumor cells by AraA also is enhanced by concurrent inhibition of adenosine deaminase. The present compound has resulted from a design of an adenosine analog which is not a substrate for adenosine deaminase. This observation that 2-fluoroadenosine is not such a substrate for adenosine deaminase led to the synthesis of 9-β-D-arabinofuranosyl-2-fluoroadenine (2-F-AraA). It has been shown that the phosphorylation of 2-F-AraA in L1210 cells in vivo revealed that the intracellular pools of 2-F-AraATP attained in L1210 cells from BDF1 mice treated with 2-F-AraA alone were comparable to levels of AraATP found in L1210 cells treated with AraA in combination with an adenosine deaminase inhibitor. The intracellular concentration of 2-F-AraATP in L1210 cells was 45, 156 and 220 nanomoles per $10^9$ cells three hours after intraperitoneal treatment with 80, 150 and 400 mg/kg of 2-F-AraA. 2-F-AraATP was not found in L1210 cells 9 and 18 hours after treatment of leukemic mice with a single dose of 80 and 150 mg/kg of 2-F-AraA, but significant levels were present 18 hours after treatment with a dose of 400 mg/kg of 2-F-AraA.

2-F-AraA inhibited DNA synthesis in L1210 cells in culture (cf. Table 1 below).

TABLE 1

Effects of 2-F-AraA (NSC-118218) on Macromolecular Synthesis in L1210 Cells in Culture

| | Treated as % of Control[a] | | | |
|---|---|---|---|---|
| | DNA[b] | | RNA[c] | Protein[d] |
| (μg/ml) | TdR-$^3$H | UR-$^3$H | UR-$^3$H | Leu-$^3$H |
| 1.0 | 102 | 84 | 135 | 119 |
| 3.0 | 49 | 36 | 163 | 86 |

TABLE 1-continued
Effects of 2-F-AraA (NSC-118218) on Macromolecular Synthesis in L1210 Cells in Culture

| (μg/ml) | DNA[b] | | RNA[c] | Protein[d] |
|---|---|---|---|---|
| | TdR-$^3$H | UR-$^3$H | UR-$^3$H | Leu-$^3$H |
| 10.0 | 18 | 11 | 137 | 66 |

[a]Inhibitor was added to L1210 cells growing in culture; radioactive substrate was added 30 min. later. These data are based on samples taken 4 hrs after addition of radioactive substrate to culture medium.
[b]Incorporation of [C$^3$H$_3$]-thymidine or [5-$^3$H]-uridine into DNA.
[c]Incorporation of [5-$^3$H]-uridine into RNA.
[d]Incorporation of [4,5-$^3$H]-L-leucine into protein.

Protein synthesis was less affected and RNA synthesis was not inhibited under the same experimental conditions. DNA synthesis in L1210 cells in vivo was markedly inhibited (10 to 20% of controls) for a period of 6-hours after treatment with 2-F-AraA (80 mg/kg).

Relative to activity against leukemia and antiviral activity, the following summation was found: Levels of F-AraATP in acid-soluble extracts prepared from L1210 and P388 leukemia cells in mice treated with 2-F-AraA (80 mg/kg) were determined by HPLC. F-AraATP (30–50 nmoles/gm cells) was present 1 to 6 hours after treatment but none was detected 9 hours after treatment. Inhibition of DNA synthesis by 2-F-AraA (80 mg/kg) in L1210 and P388 leukemia cells in vivo was pronounced for 7 hours after treatment. DNA synthesis was 90% inhibited in L1210 cells in culture by 2-F-AraA (10 μg/ml); RNA synthesis was generally not inhibited and protein synthesis was 30% inhibited. 2-F-AraA was effective against P388 leukemia; % increase in median life span of mice treated with 80 and 52 mg/kg (q3hrsx8; days 1,5,9 after implant of 10$^6$ cells) was 170% and 150%. 2-F-AraA is of importance as an anticancer agent since (a) it is not deaminated and therefore an inhibitor of ADA is not required, (b) it is phosphorylated to F-AraATP, (c) it inhibits DNA synthesis in murine leukemias, and (d) it produces significant increases in life span of mice bearing P388 leukemia.

EXAMPLE 1

2,5-Diazido-9-(2,3,5-tri-O-benzyl-β-D-arabinofuranosyl)purine (IV)

A solution of NaN$_3$ (1.16 g, 17.8 mmol) in H$_2$O (6.6 ml) was added with stirring to a solution of 2,6-dichloro-9-(2,3,5-tri-O-benzyl-β-D-arabinofuranosyl)-purine (4.8 g, 8.1 mmol) in EtOH (100 ml). After refluxing for 1 hr, the reaction mixture was filtered to remove the precipitate that formed, and the filtrate was evaporated to dryness in vacuo. Trituration of the residue with C$_6$H$_6$ (50 ml) gave a mixture from which the remaining inorganic salts were removed by filtration. Evaporation of the filtrate to dryness in vacuo gave IV as a glass: yield 4.8 g (98%), $\overline{v}_{max}$ (cm$^{-1}$) 3085, 3060, 3025, 2920, 2860 (CH), 2160, 2125 (N=N), 1595, 1565 (C=C, C=N), 1110–1065, 1020 (COC), 730, 680 (phenyl).

EXAMPLE 2

A.

2-Amino-9-(2,3,5-tri-O-benzyl-β-D-arabinofuranosyl)adenine (III)

Pd-C (5%) (500 mg) was added to a solution of 2,6-diazido-9-(2,3,5-tri-O-benzyl-β-D-arabinofuranosyl)purine (IV, 4.8 g, 8.0 mmol) in EtOH (500 ml), and the resulting mixture was hydrogenated at atmospheric pressure for 6 hr. The H$_2$ atmosphere was changed after 30 min. and after 1 hr. The catalyst was removed by filtration and was washed with CHCl$_3$ to dissolve precipitated product. The combined filtrate and washings were evaporated to dryness in vacuo, and the resulting residue was dissolved in boiling EtOH (80 ml). The crystals that formed on cooling the EtOH solution were collected by filtration, washed with EtOH, and dried in vacuo; yield 3.3 g (75%), mp 161°–162°, TLC (19:1 CHCl$_3$—MeOH). The analytically pure produce was obtained from a previous preparation: yield 69%; mp 162°; [α]$_D^{25}$+44.4±0.7° (c, 1.06, CHCl$_3$); $\lambda_{max}$ ]Mμ (ε×10$^{-3}$)], pH 1—254 (10.9), 292 (9.0); EtOH—256 (10.8), 283 (9.0); pH 7, 13—256 (9.0), 279 (9.1); $\overline{v}_{max}$ (cm$^{-1}$)3460, 3350, 3310, 3140 (NH, CH), 2940, 2915 2890, 2865 (CH), 1660 (NH), 1590 (C=C, C=N), 1085, 1045, 1015 (COC), 730, 690 (phenyl).

B.

2-Amino-9-(2,3,5-tri-O-benzyl-β-D-arabinofuranosyl)adenine (III)

Dry HCl gas was bubbled into a solution of 2,3,5-tri-O-benzyl-1-O-p-nitrobenzoyl-β-D-arabinofuranose (17 g, 30 mmol) in CH$_2$Cl$_2$ (187 ml) at −10°–0° for 2½ hr. The precipitated p-nitrobenzoic acid was removed by filtration and washed with CH$_2$Cl$_2$. The CH$_2$Cl$_2$ solution was evaporated in vacuo. The residue, dissolved in 500 ml of ethylene chloride, was added to a mixture of 2.6-diacetamidopurine (7.03 g, 30 mmol) and molecular sieve (Linde 4A, 75 g) in 500 ml of ethylene chloride. This mixture was refluxed until all the chlorosugar was consumed (TLC) (8–11 days). The mixture was then stirred with Celite and filtered. The solid was washed with CHCl$_3$, and the combined filtrates were evaporated to dryness in vacuo. The residue was dissolved in benzene and filtered (to remove unreacted 2,6-diacetamidopurine). The filtrate was again evaporated to dryness in vacuo and the residue dissolved in 100 ml of 1 N methanolic NaOMe. After a 3-hr reflux period, the solution was chilled, neutralized with acetic acid, and refrigerated overnight. The solid that precipitated was removed by filtration, washed with MeOH, and dried in vacuo; yield 5.6 g (34%); mp 159°–161°; TLC homogenous.

EXAMPLE 3

A.

9-(2,3,5-Tri-O-benzyl-β-D-arabinofuranosyl)-2-fluoroadenine (II)

HBF$_4$ (48%) (150 ml) was added to a solution (5°) of 2-amino-9-(2,3,5-tri-O-benzyl-β-D-arabinofuranosyladenine) (III, 4.6 g, 8.4 mmol) in CHCl$_3$ (60 ml). The resulting mixture was cooled to −10° before a solution of N—NO$_2$ (17 g, 25 mmol) in 4 ml of H$_2$O was added dropwise with stirring. After the addition was complete, the mixture was stirred an additional 40 min. at −10° to −5° before it was diluted with CHCl$_3$ (75 ml), cooled to −20°, and neutralized (pH 5–6) with 50% NaOH. The CHCl$_3$ layer was separated, washed with H$_2$O, dried (MgSO$_4$), and evaporated to dryness in vacuo. The residue, primarily a mixture of II and 9-(2,3,5-tri-O-benzyl-β-D-arabinofuranosyl)-2,6-difluoropurine, identified by TLC (1:1 CHCl$_3$-EtOAc), was dissolved in absolute EtOH, and the solution was saturated at 5° with dry NH$_3$. After refrigeration overnight, the reaction solution was evaporated to dryness in vacuo. The residue was dissolved in CHCl$_3$ (25 ml), and the solution was filtered through dry Celite to remove inorganic salts. The filtrate was adsorbed on a silica gel column (2.6×35 cm, packed and equilibrated with CHCl$_3$). The column was eluted with 1:1 CHCl$_3$-EtOAc. The fractions containing II were combined and evaporated to dryness in vacuo, and the residue was recrystallized from C$_6$H$_6$ (40 ml); yield 1.7 g (36%); mp 157°–159°; $\lambda_{max}$ (mμ), pH 1, 7, 13, and EtOH—261, 272 (sh); $\overline{v}_{max}$ (cm$^{-1}$) 3350, 3320, 3150 (NH), 2940, 2920, 2910, 2860 (CH), 1665, 1610, 1575 (NH, C=C, C=N), 1110, 1100, 1085, 1060 (COC), 730 (phenyl).

B.
9-(2,3,5-Tri-O-benzyl-β-D-arabinofuranosyl)-2-fluoroadenine (II)

To a solution of 2-amino-9-(2,3,5-tri-O-benzyl-β-D-arabinofuranosyl)adenine (14.5 g, 26.2 mmol) in a mixture of 500 ml tetrahydrofuran and 1 l. of 48% fluoboric acid at −15° in a 4-l. beaker equipped with a mechanical stirrer was added dropwise in 20 min a saturated aqueous solution of NaNO$_2$ (7.2 g, 105 mmol). The addition of NaNO$_2$ (5.4 g, 78.6 mmol) was repeated three times after which none of the 2-aminoadenine remained (TLC). The fluoroboric acid was neutralized with 50% NaOH keeping the temperature between −40 and 0°. The solution was extracted four times with CHCl$_3$ (300 ml, 250 ml, and two 200-ml portions). The CHCl$_3$ extract was washed with saturated NaCl solution and then dried over MgSO$_4$ before it was evaporated to dryness in vacuo. The residual oil was dissolved in a liter of ethanolic NH$_3$ (saturated at 0°), and the solution was allowed to stand for three days at 0° before it was evaporated to dryness. The residue was recrystallized from 100 ml EtOH; yield 4.7 g. Additional material was recovered from the filtrate by recrystallization and preparative TLC. The total yield was 5.8 g (40%).

EXAMPLE 4

A. 9-β-D-Arabinofuranosyl-2-fluoroadenine (I)

9-(2,3,5-tri-O-benzyl-β-D-arabinofuranosyl)-2-fluoroadenine (II, 1.7 g, 3 mmol) was suspended in liquid NH$_3$ (75 ml) with stirring and Na (410 mg, 18 g-atoms) was added in small portions. When a purple color persisted for a few minutes after the addition of Na, the mixture was neutralized with NH$_4$Cl (920 mg, 18 mmol). The NH$_3$ was evaporated in a stream of dry N$_2$, and the residue was triturated with Et$_2$O (75 ml). The insoluble solid that formed was collected by filtration and washed with H$_2$O (three 3-ml portions) before it was recrystallized from H$_2$O (65 ml) giving the crude produce (479 mg), which was shown by TLC (4:1 CHCl$_3$-MeOH) to be primarily a mixture of I and 9-β-D-arabinosyladenine. A solution of the crude product in H$_2$O (1 ml/mg) was percolated through an ion-exchange column [10 g of Amberlite (CG50, 100–200 Mexh)/mmol of nucleoside] at a rate not exceeding 0.5 ml/min, and the column was eluted with H$_2$O until elution of I was complete. The fractions containing homogeneous I were combined and evaporated to dryness. The residue was recrystallized from H$_2$O; yield 290 mg (34%), mp 265°–267° (Mel-Temp).

An analytically pure sample was obtained from a previous synthesis. The crude produce was first purified by TLC, and pure I was obtained after three recrystallizations (EtOH-H$_2$O) of the TLC-isolated material: mp 260° (Mel-Temp); $[\alpha]_D^{25}$ +17.0±2.5° (c 0.1, EtOH); $\lambda_{max}$ [mμ ($\epsilon \times 10^{-3}$)], pH 1—262 (13.2); pH 7—261 (14.8); pH 13—262 (15.0); $\overline{v}_{max}$ (cm$^{-1}$) 3450, 3305, 3180, 3025 (OH, NH), 2915, 2900 (CH), 1630 (NH), 1610, 1590 (C=C, C=N), 1115, 1085, 1055, 1020, 1000 (COC); δ[ppm (DMSO-d$_6$)] 3.70 m (two 5′-H and 4′-H), 4.13 m (3′-H and 2′-H), 4.98 (5′-OH), 5.5 m (2′-OH and 3′-OH), 6.13 (d, J$_{1'2'}$=4.2 Hz, 1′-H), 7.2 broad (NH$_2$), 8.16 (8-H).

B. 9-β-D-Arabinofuranosyl-2-fluoroadenine (I)

BCl$_3$ gas (72.9) was bubbled in CH$_2$Cl$_2$ (610 ml) at 0° in a 2-l., 3-necked flask equipped with a thermometer, magnetic stirrer, and addition funnel and the stirred solution then cooled to −72° (dry ice-acetone) before the dropwise addition (1 hr) of a cold solution of 9-(2,3,5-tri-O-benzyl-β-D-arabinofuranosyl)-2-fluoroadenine (II, 7.0 g, 12.5 mmol) in CH$_2$Cl$_2$ (70 ml). After a total reaction time of 2¾ hr, the cooling bath was removed and the solvent and gas removed in vacuo. The residue was dissolved in CH$_2$Cl$_2$ (40 ml) and the solution evaporated to dryness (six times), or until a solid white residue is obtained, before adding 450 ml of 5% NaHCO$_3$ followed by solid NaHCO$_3$ to adjust the pH to 6–7. The mixture was diluted with EtOH, heated to boiling, treated with charcoal, filtered through Celite, and then allowed to stand at room temperature overnight. It was then chilled and the solid collected by filtration, washed with cold H$_2$O and then ether, and dried in vacuo; yield 3.23 g (91%); mp 259°–260°; homogeneous according to TLC (19:1) and HPLC (23 H$_2$O:2 MeCN); pmr; 3.7 (m, H$_{4'}$ and 2H$_{5'}$), 4.15 (m, H$_{2'}$ and H$_{3'}$), 5.1 (t, 5′-OH), 5.55 and 5.65 (2d, 2′-OH and 3′-OH), 6.14 (d, J$_{1'2'}$ 3Hz, H$_{1'}$), 7.8 (broad s, NH$_2$), 8.2 (s, H$_8$); uv: pH 1—262 (13.2); ph 7, 13—261 (15.3).

EXAMPLE 5

TABLE 2

| | | Therapeutic Activity of 2-F-AraA Against Leukemia L1210[a] | | | |
|---|---|---|---|---|---|
| | 2-F-AraA Treatment | | Median Day of Death | | Estimated No. L1210 Cells |
| Expt. | mg/kg/dose[b] | Schedule; Route[c] | (Dying Mice Only) Treated/Control | Median % ILS[d] | 60-Day Survivors | Surviving Therapy[e] |
| 1 | 100 | q3h × 8, days 1,5,9; i.p. | 19/8.5 23/9 | 123 155 | 2/6 1/6 | 4 × 10$^4$ (1.1) 5 × 10$^2$ (1.8) |
| 2 | 100 | q6h × 4, days 1,5,9; i.p. | 16.5/9 | 83 | 0/6 | 3 × 10$^6$ |
| 2 | 400 | q12h × 2, days 1,5,9; i.p. | 22/9 | 144 | 1/6 | 2 × 10$^3$ (1.8) |
| 2 | 150 | q3h × 8, days | 15/9 | 66 | 0.6 | 2 × 10$^7$ |

TABLE 2-continued

Therapeutic Activity of 2-F-AraA Against Leukemia L1210[a]

| Expt. | 2-F-AraA Treatment mg/kg/dose[b] | Schedule; Route[c] | Median Day of Death (Dying Mice Only) Treated/Control | Median % ILS[d] | 60-Day Survivors | Estimated No. L1210 Cells Surviving Therapy[e] |
|---|---|---|---|---|---|---|
| | | 1,5,9; oral | | | | |

[a]$10^5$ L1210 ascites cells implanted i.p. on day 0.
[b]Treatments reported were selected from a range of dose levels from lethally toxic to apparently nontoxic. Those included here resulted in no more than 16% (1/6 treated mice) dying without gross evidence of progressive leukemia (splenomegaly), except those treated orally, in which the dose range tested contained no toxic levels.
[c]i.p. = intraperitoneal; oral = drug administered directly into stomach by catheter.
[d]% ILS = % increase in life span, compared to untreated control; excluding 60-day survivors.
[e]Based on median day of death in dying animals only. Figures in parentheses based on % survivors.

AraA, in the absence of adenosine deaminase inhibitors, has no significant therapeutic activity against L1210 leukemia. Since 2-F-AraA is not deaminated it was tested alone in BDF1 mice implanted i.p. with $10^5$ L1210 cells. 2-F-AraA was given i.p. or orally on the basis of average mouse body weight. Therapeutic activity based on observed increase in median life span of treated animals over untreated controls and on estimates of the number of viable L1210 cells present at the end of treatment is summarized in Table 2. The data presented show that 2-F-AraA has reproducible therapeutic activity against L1210 and, in agreement with the observed maintenance of 2-F-AraATP levels in L1210 cells following a single dose of 400 mg/kg of 2-F-AraA, that repeated doses of the drug at short intervals are not required for optimal therapeutic activity. 2-F-AraA has some therapeutic activity against L1210 following oral administration.

The findings show (a) that 2-F-AraA is not a substrate for adenosine deaminase; (b) that it is phosphorylated to 2-F-AraATP; (c) that it inhibits DNA synthesis in L1210 cells in culture and in vivo; and (d) that 2-F-AraA alone is therapeutically effective against L1210 leukemia.

EXAMPLE 6

TABLE 3

IN VITRO ANTIVIRAL ACTIVITY OF 2-FLUORO-ARA-A (NSC 118218)

Virus Rating (VR)[*][+]

| DNA Viruses | | | RNA Viruses | |
|---|---|---|---|---|
| Herpes Simplex Virus Type 1 | Vaccinia Virus | Human Cytomegalovirus | Rhinovirus Type 1A | Parainfluenza Virus Type 3 |
| 1.4 | 1.3 | 0.3 | 0 | 0 |

[*]Virus Rating (VR): A weighted measurement of antiviral activity which takes into account the degree of virus-specific cytopathogenic effect (cpe)-inhibition, toxicity, and virus concentration, as determined by a modification of the methods of Ehrlich et al. (Ann. N.Y. Acad. Sci. 140:7, 1965). In our experience, a VR≧1.0 indicates definite antiviral activity; a VR of 0.5-0.9 indicates moderate antiviral activity; and a VR ≦0.5 indicates no significant antiviral activity.
[+]Average VR adjusted for number of Microtiter wells employed.

I claim:
1. A method of treating murine leukemias L1210 and P388 by medicating orally or intraperitoneally leukemic mice with 9-β-D-arabinofuranosyl-2-fluoroadenine, a metabolically stable drug, given over a treatment span of 1-10 days with dosage repeated 2-8 times per diem.
2. The method according to claim 1 wherein the treatment dosage is 8-400 mg/kg/dose on a 10-day treatment of from 2-8 times per day at days 1, 5, and 9.
3. The method according to claim 2 wherein the daily dosage is given as a unit.
4. The method according to claim 1 wherein the murine leukemia is L1210.
5. The method according to claim 1 wherein the murine leukemia is P388.
6. A method of treating DNA virus infections, exemplified by infections with herpes simplex virus and vaccinia virus grown in HEp-2 cells, with an antiviral dosage of 9-β-D-arabinofuranosyl-2-fluoroadenine.

* * * * *